United States Patent
Cen et al.

(10) Patent No.: US 12,371,439 B2
(45) Date of Patent: Jul. 29, 2025

(54) CRYSTALLINE FORM B OF TETRAHYDROTHIENOPYRIDINE COMPOUND, PREPARATION METHOD, COMPOSITION AND APPLICATION THEREOF

(71) Applicant: Chengdu Shibeikang Biomedical Technology Co. Ltd., Sichuan (CN)

(72) Inventors: Guodong Cen, Sichuan (CN); Maoting Yang, Sichuan (CN); Shaojun Tan, Sichuan (CN)

(73) Assignee: Chengdu Shibeikang Biomedical Technology Co. Ltd., Sichuan (CN)

( * ) Notice: Subject to any disclaimer, the term of this patent is extended or adjusted under 35 U.S.C. 154(b) by 684 days.

(21) Appl. No.: 17/750,688

(22) Filed: May 23, 2022

(65) Prior Publication Data
US 2022/0289761 A1 Sep. 15, 2022

Related U.S. Application Data

(63) Continuation of application No. PCT/CN2020/081091, filed on Mar. 25, 2020.

(30) Foreign Application Priority Data

May 17, 2019 (CN) .............................. 201910412233

(51) Int. Cl.
C07D 495/04 (2006.01)
(52) U.S. Cl.
CPC ........ *C07D 495/04* (2013.01); *C07B 2200/13* (2013.01)
(58) Field of Classification Search
CPC .............................. C07D 495/04; C07B 2200/13
See application file for complete search history.

(56) References Cited

U.S. PATENT DOCUMENTS

2012/0329762 A1 12/2012 Kumar et al.
2013/0165476 A1* 6/2013 Sun ........................... A61P 9/10
  546/114

FOREIGN PATENT DOCUMENTS

CN 104245707 12/2012
CN 108685913 10/2018

OTHER PUBLICATIONS

Chinese Pharmacopoeia, 2015 edition, "High Performance Liquid Chromatography," General Chapter 0512, vol. 4, 27 pages.
Chinese Pharmacopoeia, 2015 edition, "Thermal Analysis," General Chapter 0661, vol. 4, 6 pages.
Chinese Pharmacopoeia, 2015 edition, "X-ray Diffraction Method," Method 2 of General Chapter 045, vol. 4, 5 pages.
Farid et al., "Metabolism and disposition of the thienopyridine antiplatelet drugs ticlopidine, clopidogrel, and prasugrel in humans," J Clin . Pharmacol, Feb. 2010, 50:126-142, Abstract.
Office Action in Chinese Appln. No. 201910412233.5, mailed Oct. 26, 2022, 27 pages (with English translation).
Peng, "Pharmaceutical Analysis," China Pharmaceutical Science and Technology Press, Jul. 31, 2018, p. 36.
Shaw et al., "Synthesis of Biologically Active Piperidine Metabolites of Clopidogrel: Determination of Structure and Analyte Development," The Journal of Organic Chemistry, 2015, 80(14):7019-7032.
Zhen, "Pharmaceutical Analysis," Traditional Medicine Press, Jan. 2000, p. 40.

* cited by examiner

*Primary Examiner* — Timothy R Rozof
(74) *Attorney, Agent, or Firm* — Fish & Richardson P.C.

(57) ABSTRACT

Disclosed in the present invention are a crystalline form B of a tetrahydrothienopyridine compound having a structure as represented by Compound I, a preparation method, a composition and an application thereof, for use in solving the problems in the prior art of lots of impurities, low content, bad crystalline form stability, and inability to form a drug. The crystalline form B uses Cu-Kα radiation, and X-ray powder diffraction expressed at a 2θ angle has characteristic peaks at 11.21±0.2°, 12.61±0.2°, 14.69±0.2°, 16.14±0.2°, 17.81±0.2°, 20.22±0.2°, and 22.10±0.2°. The crystalline form B of the present invention has few of impurities, good stability, good crystallinity, and reproducibility, and is suitable for industrial production. Moreover, the crystalline form B has an unexpectedly stronger anti-ADP-induced platelet aggregation effect and better fluidity.

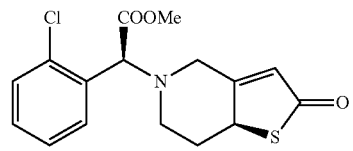

18 Claims, 4 Drawing Sheets

CRYSTALLINE FORM B OF TETRAHYDROTHIENOPYRIDINE COMPOUND, PREPARATION METHOD, COMPOSITION AND APPLICATION THEREOF

TECHNICAL FIELD

The present invention belongs to the technical field of medicinal chemistry, and particularly relates to a crystalline form B of a tetrahydrothienopyridine compound, methyl (S)-2-(2-chlorophenyl)-2-((S)-2-oxo-2,6,7,7a-tetrahydrothieno[3,2-c]pyridin-5(4H)-yl)acetate, and a preparation method, composition and application thereof.

TECHNICAL BACKGROUND

According to the data from China Cardiovascular Disease Report 2017, the prevalence and mortality of cardiovascular disease (CVD) in China have been on the rise in recent years. It is estimated that there are 290 million people suffering from CVD, including 13 million people suffering from stroke, 11 million people suffering from coronary heart diseases, 4.5 million people suffering from heart failure and 270 million people suffering from hypertension. The latest survey data published in "JAMA Cardiology" showed that the total number of deaths due to CVDs was as high as 3.97 million people in China in 2016, accounting for more than 40% of the total number of deaths due to diseases among the population, which has become the leading cause of death due to diseases in China and is higher than the number of deaths due to tumors. Cardiovascular and cerebrovascular thrombotic diseases, such as ischemic stroke (IS) and hemorrhagic stroke (HS), are the most predominant and highly lethal diseases. Furthermore, a recently completed cross-sectional study on the burden of stroke in China conducted by Ness-China showed that the crude rate of stroke incidence had reached an alarming level of 345.1 cases per 100,000 people per year in China by 2013, indicating that China has now become a country with a high incidence of thrombosis diseases. Therefore, the prevention, control and treatment of cardio-cerebral thrombotic diseases are particularly important in this severe situation.

The key physiological pathway of thrombosis is platelet adhesion and aggregation. Therefore, platelet aggregation inhibitors play an important role in the treatment of thrombotic diseases, and have been the focus of research. Clopidogrel (Plavix) from Sanofi S.A., as one of the most representative anticoagulant drugs, is widely used in the current clinical first-line treatment and prevention of thrombotic diseases due to its good safety and rapid inhibition of platelet aggregation. Unfortunately, the application of clopidogrel is limited due to significant individual differences in efficacy of clopidogrel, particularly in Asians, namely, clopidogrel resistance (CPGR). Farid et al. conducted a detailed and comprehensive study on the metabolism of clopidogrel in vivo in 2010 (J. Clin. Pharmacol 2010; 50:126-142), revealing that the cause of CPGR is due to individual differences in CYP enzyme activity in the liver, which is manifested by the fact that clopidogrel cannot be metabolized normally in the liver of some patients, and cannot produce metabolites having the structure of Formula I and their optical isomers, thereby blocking clopidogrel from being subsequently further metabolized to an active ingredient and the inability to exert anticoagulant action. The chemical name of the compound of formula I is methyl (S)-2-(2-chlorophenyl)-2-((S)-2-oxo-2,6,7,7a-tetrahydrothieno[3,2-c]pyridin-5(4H)-yl)acetate.

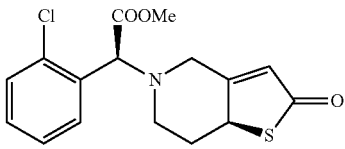

Formula I

According to this metabolic pathway, pharmaceutical researchers have carried out a series of structural optimizations of clopidogrel in the hope of overcoming CPGR, but unfortunately, many bold attempts, including vicagrel and prasugrel, have failed to achieve satisfactory results due to the side effects associated with structural modifications. On the other hand, the IPCA laboratory in India heuristically and simply disclosed a method for preparing a compound of the structural Formula I and a preliminary study on the druggability thereof through the patent No. CN 104245707. Since the compound is a normal CYP enzyme metabolite of clopidogrel, it is foreseen that the compound would be able to overcome CPGR and minimize other uncontrollable risks associated with the structural changes while inheriting the traditional efficacy of clopidogrel. However, unfortunately, the patent does not thoroughly study a crystalline form of the compound, but merely selectively precipitates a crystalline form of the compound having the structural formula I through a racemic mixture. This crystalline form has a higher chiral purity than diastereomers, but has many other impurities, low content, poor crystalline stability and no druggability.

It is well known for a person skilled in the art that the crystalline structure of a pharmaceutically active ingredient often affects the chemical stability of a drug, and that differences in crystallization conditions and storage conditions may lead to changes in the crystalline structure of the compound, sometimes accompanied by the production of other crystalline forms, thereby affecting the stability, water solubility, storage, etc., of the pharmaceutical formulation, thereby affecting the safety and reliability of the drug. Therefore, it is necessary to conduct a thorough research on crystalline forms of the compound of formula I. The provision of a crystalline form of the compound of formula I that is highly stable, safe, and suitable for industrial production and has a good prospect of becoming a drug, has become an urgent problem to be solved by a person skilled in the art.

SUMMARY OF THE INVENTION

One of the objects of the present invention is to provide a crystalline form B of a tetrahydrothienopyridine compound having the structure represented by formula I, methyl (S)-2-(2-chlorophenyl)-2-((S)-2-oxo-2,6,7,7a-tetrahydrothieno[3,2-c]pyridin-5(4H)-yl)acetate, to solve problems of many impurities, low content, poor crystalline stability and no druggability in the prior art.

A second object of the present invention is to provide a preparation method of the crystalline form B.

A third object of the present invention is to provide a pharmaceutical composition comprising the crystalline form B.

A fourth object of the present invention is to provide an application of the crystalline form B.

In order to achieve the above objects, the technical solution of the present invention is provided as follows:

A crystalline form B of a tetrahydrothienopyridine compound having the structure represented by formula I of the present invention has characteristic peaks at 2θ angles of 11.21±0.2°, 12.61±0.2°, 14.69±0.2°, 16.14±0.2°, 17.81±0.2°, 20.22±0.2°, and 22.10±0.2° degrees in an X-ray powder diffraction pattern with Cu-Kα radiation.

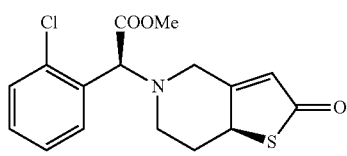

Formula I

In one embodiment, the crystalline form B has characteristic peaks at 2θ angles of 11.21±0.2°, 12.61±0.2°, 14.69±0.2°, 16.14±0.2°, 17.81±0.2°, 20.22±0.2°, 22.10±0.2°, 23.24±0.2°, 27.68±0.2°, and 28.57±0.2° degrees in an X-ray powder diffraction pattern with Cu-Kα radiation.

In one embodiment, the crystalline form B has characteristic peaks at 2θ angles of 11.21±0.2°, 12.61±0.2°, 14.69±0.2°, 16.14±0.2°, 17.81±0.2°, 19.42±0.2°, 20.22±0.2°, 20.76±0.2°, 22.10±0.2°, 23.24±0.2°, 24.31±0.2°, 27.01±0.2°, 27.68±0.2°, 28.57±0.2°, and 31.09±0.2° degrees in an X-ray powder diffraction pattern with Cu-Kα radiation.

In one embodiment, the crystalline form B has an X-ray powder diffraction pattern as shown in FIG. 1.

In one embodiment, a differential scanning calorimetry spectrogram of the crystalline form B has an endothermic peak at 151.71±5° C.

In one embodiment, the differential scanning calorimetry spectrogram of the crystalline form B is shown in FIG. 2.

According to the thermogravimetric analysis (TGA), the crystalline form B of the present invention has no significant weight loss before 100° C. and between 100° C. and 170° C., indicating that the crystalline form does not contain volatile solvents, adsorbed water and crystal water.

In one embodiment, the thermogravimetric analysis spectrogram of the crystalline form B is shown in FIG. 3.

In a preferred embodiment of the present invention, a single crystal structure of the compound of formula I is provided. According to X-ray single crystal diffraction data, the crystal has a monoclinic crystal system, which belongs to a space group P21, and has lattice constants a=6.7206(5) Å, b=15.2446(9) Å, c=8.0941(5) Å, α=90°, β=102.618(6°), and γ=90°. The single crystal of the crystalline form B has an X-ray single crystal diffraction pattern as shown in FIG. 4.

A method for preparing the crystalline form B of the compound of formula I according to the present invention comprises dissolving a crude product of the compound of formula I in any crystalline form or amorphous form in a solvent in any manner, then cooling or concentrating to crystallize, filtering, washing and drying the resulting solid to obtain the crystalline form.

The crude product of the compound of formula I means that a mass content of the compound of formula I is less than 98%.

The solvent is selected from any one or more of alcohols, ketones, nitriles, ethers, esters and sulfones with the number of carbon atoms less than 7 or equal to 7, or a mixed solvent of any one or more thereof and water.

Preferably, the alcohols include methanol, ethanol, isopropanol, 1-propanol, 2-propanol, 1-butanol, 2-butanol and pentanol. The ketones include acetone, methyl ethyl ketone and methyl isopropyl ketone. The nitriles include acetonitrile. The ethers include diethyl ether, isopropyl ether, methyl tert-butyl ether and anisole. The esters include methyltetrahydrofuran, ethyl formate, ethyl acetate, propyl acetate, butyl acetate, isopropyl acetate and isobutyl acetate. The sulfones include dimethyl sulfoxide.

The condition of cooling crystallization is standing crystallization at −20° C. to room temperature.

The condition of concentration crystallization is that the solvent is concentrated by a rotary evaporator at an external temperature of 35° C. for crystallization.

In some specific embodiments, the filter cake is washed with an ice-cold corresponding crystallization solvent, preferably a corresponding crystallization solvent at 0° C.

The drying is air-drying at 35° C. under atmospheric pressure.

A pharmaceutical composition of the present invention comprises the crystalline form B of the above-mentioned compound and one or more pharmaceutically acceptable carriers. The "pharmaceutically acceptable carrier" refers to a diluent, adjuvant, excipient or vehicle administered with a therapeutic agent, which is, within the scope of reasonable medical judgment, suitable for contact with the tissues of humans and/or other animals without excessive toxicity, irritation, allergic responses, or other problems or complications corresponding to a reasonable benefit/risk ratio.

Use of the crystalline form B of the compound of formula I of the present invention in the preparation of a medicament for the prevention or treatment of cardiac, cerebral and other arterial circulation disorders due to platelet hyperaggregation is provided. Such other arterial circulation disorders include stroke, acute coronary syndrome, atherosclerosis, myocardial infarction and confirmed peripheral arterial diseases.

Compared with the prior art, the present invention has the following beneficial effects.

The present invention has creatively found that the refined crystallization of the crude product of the compound of formula I, methyl (S)-2-(2-chlorophenyl)-2-((S)-2-oxo-2,6,7,7a-tetrahydrothieno[3,2-c]pyridin-5(4H)-yl)acetate, in a single isomeric form, affords a crystalline form, i.e., Form B, having excellent advantages, such as few impurities, good stability, good crystallinity, reproducibility and operability. Moreover, the preparation method of the crystalline form B is simply operated using a controllable, cheap and easily available solvent under mild crystallization conditions, and the resulting crystalline form is stable, and suitable for industrial production.

In addition, the crystalline Form B also has unexpected technical effects: it has a more potent anti-ADP-induced platelet aggregation effect, which is significantly different from the crystalline forms reported in the prior art, and is an advantageous crystalline form with potential for further medicinal development. In addition, the crystalline form B also has unexpectedly better flowability, which allows the crystalline form B to have better tableting performance and be more favorable for the control of the tablet weight variation of a finished product, thereby further ensuring the efficacy and safety of administration.

DETAILED DESCRIPTION OF THE INVENTION

Figure 1:
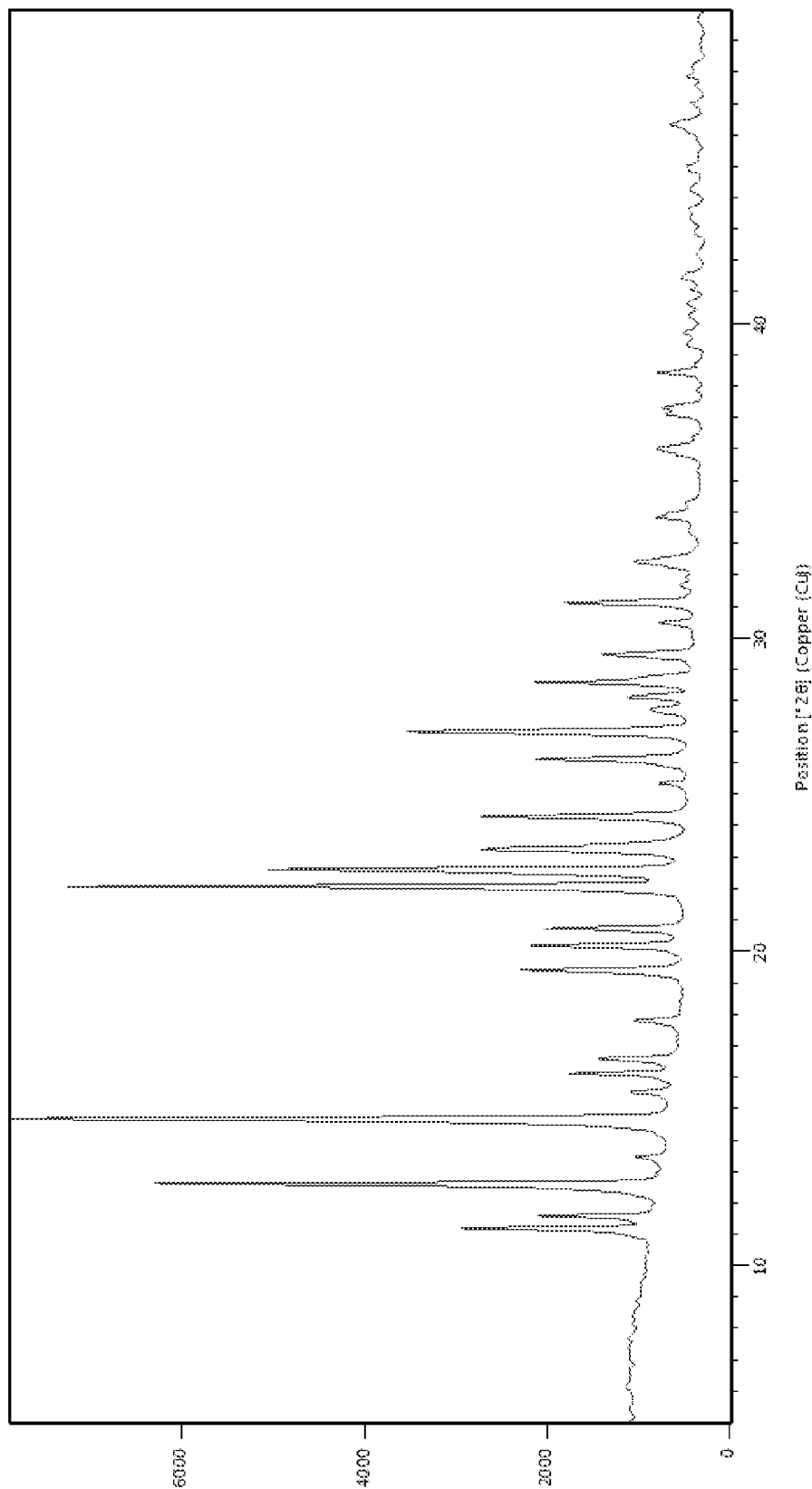
FIG. 1 shows an XRPD pattern of the crystalline form B of the compound of formula I.

The technical solution of the present invention is illustrated below with specific examples. However, the protection scope of the present invention is not limited to the examples described herein. All reagents used are commercially available products.

In the examples of the present invention, according to Method 2 of General Chapter 0451 X-ray Diffraction Method in *Chinese Pharmacopoeia* (2015 Edition) Volume IV, X-ray powder diffraction spectra of samples were measured using Empyrean X-ray powder diffractometer of PANalytical B.V. under the following conditions: monochromatic Cu-Kα rays (λ=1.5418 Å), scanning mode: 0/2θ, scanning range: 0-50°, tube voltage: 35 kV, tube current: 30 mA, and scanning speed: 8°/min.

In the examples of the present invention, according to General Chapter 0661 Thermal Analysis in *Chinese Pharmacopoeia* (2015 Edition) Volume IV, DSC spectrograms of the samples were measured using TA Instruments Q20 Differential Scanning Calorimeter under the following conditions: purge gas: nitrogen, initial temperature: 0° C., final temperature: 200° C., and heating rate: 20° C./min.

In the examples of the present invention, according to General Chapter 0661 Thermal Analysis in *Chinese Pharmacopoeia* (2015 Edition) Volume IV, TGA spectrograms of the samples were measured using TA Instruments TGA Q500 Thermogravimetric Analyzer under the following conditions: purge gas: nitrogen, initial temperature: 0° C., final temperature: 800° C., and heating rate: 20° C./min.

In the examples of the present invention, according to Method 1 of General Chapter 0451 X-ray Diffraction Method in *Chinese Pharmacopoeia* (2015 Edition) Volume IV, X-ray single crystal diffraction spectra of the samples were measured using Empyrean X-ray powder diffractometer of PANalytical B.V. under the following conditions: monochromatic Cu-Kα rays (λ=1.5418 Å), scanning mode: 0/2θ, scanning range: 0-50°, tube voltage: 35 Kv, and tube current: 30 mA.

A person skilled in the art should understand that, various characterization data of the crystalline form according to the present invention are affected by various factors, such as detection equipments and conditions, and therefore, the peak positions or relative intensities of the measured X-ray powder diffraction patterns may be varied to a certain extent. When determining whether a crystalline form is the same as a known crystalline form, more attention should be paid to the relative positions of peaks, rather than relative intensities thereof, which is also well known in the field of crystallography. It should be noted that due to changes in temperature, sample movement, or calibration of an instrument, etc., the peak positions of characteristic peaks can be shifted within an appropriate range, and the measurement error of 2θ values is generally accepted to be ±0.2°.

In addition, DSC can be used to analyze a transition temperature when a crystal absorbs or releases heat due to crystal transformation or crystal melting. For the same crystalline form of the same compound, it is well known that the error between the crystal transformation temperature and the melting point should be within 5° C. according to crystallography in a continuous analysis, and should be within 3° C. under normal circumstances.

The crude product of the single isomeric compound of formula I used in the examples of the present invention was prepared with reference to the method of Example 2 disclosed in patent No. CN 104245707.

Example 1

This example provided a preparation method of the crystalline form B of the compound of formula I of the present invention as follows.

To a 100 mL eggplant flask, 5.0 g crude product of the single isomeric compound of formula I and 40 mL acetone were added, heated to 60° C., stirred until substantially dissolved, and filtered while hot, and the filtrate was placed into a 100 mL beaker and stirred, slowly cooled to room temperature, and stirred overnight for crystallization. The resulting product was dried to obtain a 0.58 g solid, with a yield of 58%. The resulting crystal had characteristic peaks at about 11.21±0.2° (7.90), 12.61±0.2° (7.02), 14.69±0.2° (6.03), 16.14±0.2° (5.49), 17.81±0.2° (4.98), 19.42±0.2° (4.57), 20.22±0.2° (4.39), 20.76±0.2° (4.27), 22.10±0.2° (4.02), 23.24±0.2° (3.83), 24.31±0.2° (3.66), 27.01±0.2° (3.30), 27.68±0.2° (3.22), 28.57±0.2° (3.12) and 31.09±0.2° (2.88). The DSC spectrogram was shown in FIG. 2, and there was only one sharp melting endothermic peak at 151.71° C. The TGA spectrogram was shown in FIG. 3, and the resulting crystalline form was defined as crystalline form B.

Example 2

This example provided a preparation method of the crystalline form B of the compound of formula I of the present invention as follows.

Figure 4:
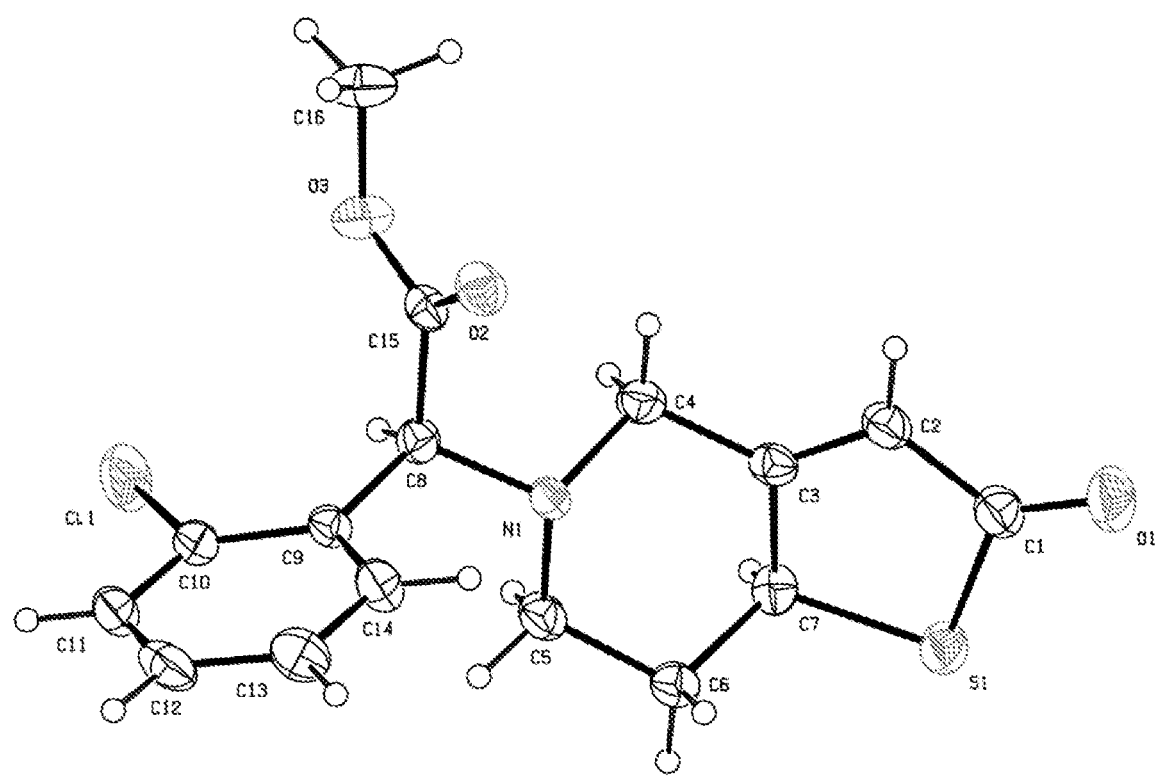
FIG. 4 shows a single crystal diffraction pattern of the crystalline form B of the compound of formula I.

To a 10 mL eggplant flask, 100 mg crude product of the single isomeric compound of formula I and 5 mL acetone were added, dissolved by shaking at 60° C., and filtered while hot, and the filtrate was placed into a clean 5 mL eggplant flask, allowed to stand slowly and cool to room temperature to obtain a single crystal of the compound of formula I with a high crystallinity, and the single crystal diffraction pattern was shown in FIG. 4. After cryogrinding of the single crystal, X-ray powder diffraction pattern and DSC spectrogram thereof were studied and compared, and the resulting product was determined to be crystalline form B.

Example 3

This example provided a preparation method of the crystalline form B of the compound of formula I of the present invention as follows.

To a 100 mL eggplant flask, 1.0 g crude product of the single isomeric compound of formula I and 35 mL acetonitrile were added, heated to 60° C., stirred until substantially dissolved, and filtered while hot, and the filtrate was placed into a 100 mL beaker and stirred, slowly cooled to room temperature, and stirred overnight for crystallization. The resulting product was dried to obtain a 0.42 g solid, with a yield of 42%. X-ray powder diffraction pattern and DSC spectrogram thereof were studied and compared, and the resulting product was determined to be crystalline form B.

Example 4

This example provided a preparation method of the crystalline form B of the compound of formula I of the present invention as follows.

To a 50 mL eggplant flask, 1.0 g crude product of the single isomeric compound of formula I and 15 mL ethanol were added, heated to 60° C., stirred until substantially dissolved, and filtered while hot, and the filtrate was placed into a 50 mL beaker and stirred, slowly cooled to room temperature, and stood at −20° C. for crystallization. The resulting product was dried to obtain a 0.45 g solid, with a yield of 45%. X-ray powder diffraction pattern and DSC spectrogram thereof were studied and compared, and the resulting product was determined to be crystalline form B.

Example 5

This example provided a preparation method of the crystalline form B of the compound of formula I of the present invention as follows.

To a 50 mL eggplant flask, 1.0 g crude product of the single isomeric compound of formula I and 20 mL diethyl ether were added, heated to 30° C., stirred until substantially dissolved, and filtered while hot, and the filtrate was placed into a 50 mL beaker and stirred, slowly cooled to room temperature, and stirred overnight for crystallization. The resulting product was dried to obtain a 0.45 g solid, with a yield of 45%. X-ray powder diffraction pattern and DSC spectrogram thereof were studied and compared, and the resulting product was determined to be crystalline form B.

Example 6

This example provided a preparation method of the crystalline form B of the compound of formula I of the present invention as follows.

To a 50 mL eggplant flask, 1.0 g crude product of the single isomeric compound of formula I and 30 mL tetrahydrofuran were added, heated to 60° C., stirred until substantially dissolved, and filtered while hot, and the filtrate was placed into a 50 mL beaker and stirred, slowly cooled to room temperature, and stirred overnight for crystallization. The resulting product was dried to obtain a 0.38 g solid, with a yield of 38%. X-ray powder diffraction pattern and DSC spectrogram thereof were studied and compared, and the resulting product was determined to be crystalline form B.

Example 7

This example provided a preparation method of the crystalline form B of the compound of formula I of the present invention as follows.

To a 50 mL eggplant flask, 1.0 g crude product of the single isomeric compound of formula I and 20 mL DMSO were added, heated to 60° C., stirred until substantially dissolved, and filtered while hot, and the filtrate was placed into a 50 mL beaker and stirred, slowly cooled to room temperature, and stirred overnight in ice bath for crystallization. The resulting product was dried to obtain a 0.28 g solid, with a yield of 28%. X-ray powder diffraction pattern and DSC spectrogram thereof were studied and compared, and the resulting product was determined to be crystalline form B.

Comparative Preparation Example 1

This example was a comparative example, and provides a preparation method of the crystalline form in the prior art (CN 104245707) as follows.

To a 100 mL eggplant flask, 1.0 g crude product of a racemic mixture (prepared according to the method of Example 1 disclosed in CN 104245707) of formula I, 30 mL ethyl acetate and 1.5 mL methanol were added, heated to 60° C., stirred until substantially dissolved, and filtered while hot, and the filtrate was placed into a 100 mL beaker and stirred, slowly cooled to room temperature, and stirred overnight for crystallization. The resulting product was dried to obtain a 0.32 g solid, with a yield of 32%. The resulting product was identified as the crystalline form described in CN 104245707 according to X-ray powder diffraction pattern comparison and melting point measurement (melting range was 135.0-138.0° C.).

Comparative Preparation Example 2

This example was a comparative example, and provides a preparation method of the crystalline form in the prior art (CN 104245707) as follows.

To a 100 mL eggplant flask, 1.0 g crude product of a racemic mixture (prepared according to the method of Example 1 disclosed in CN 104245707) of formula I, 30 mL ethyl acetate and 3 mL methanol were added, heated to 60° C., stirred until substantially dissolved, and filtered while hot, and the filtrate was placed into a 100 mL beaker and stirred, slowly cooled to room temperature, and stirred overnight for crystallization. The resulting product was dried to obtain a 0.38 g solid, with a yield of 38%. The resulting product was identified as the crystalline form described in CN 104245707 according to X-ray powder diffraction pattern comparison and melting point measurement (melting range was 134.5-138.0° C.).

Comparative Preparation Example 3

This example was a comparative example, and provides a preparation method of the crystalline form in the prior art (CN 104245707) as follows.

To a 100 mL eggplant flask, 5.0 g crude product of a racemic mixture (prepared according to the method of Example 1 disclosed in CN 104245707) of I, 30 mL ethyl acetate and 6 mL methanol were added, heated to 60° C., stirred until substantially dissolved, and filtered while hot, and the filtrate was placed into a 100 mL beaker and stirred, slowly cooled to room temperature, and stirred overnight for crystallization. The resulting product was dried to obtain a 0.41 g solid, with a yield of 41%. The resulting product was identified as the crystalline form described in CN 104245707 according to X-ray powder diffraction pattern comparison and melting point measurement (melting range was 135.0-138.0° C.).

Test 1 Determination of Related Substances in the Crystalline Forms in the Examples The crystalline forms of the compound of formula I obtained from each example and each comparative preparation example were analyzed by HPLC.

Instrument and equipment: Agilent-1100 High Performance Liquid Chromatograph;

Chromatographic conditions and system suitability test: octadecylsilane-bonded silica gel was used as a filler; water (pH adjusted to 3.8 with phosphoric acid):acetonitrile (45:55) was used as a mobile phase; detection wavelength was 220 nm; theoretical tower plate number should not be less than 2000; the resolution should not be less than 2.0; and the resolution from other adjacent impurity peaks should meet the requirements.

Test solution: an appropriate amount of the compound obtained from each example was accurately weighed, dissolved in anhydrous ethanol, and diluted quantitatively to prepare a solution containing about 1 mg compound per 1 ml solution as the test solution.

Reference solution: 1 ml of reference solution of the compound of formula I was accurately measured, and placed into a 100 ml volumetric flask, diluted with anhydrous ethanol to the scale, and shaken well to obtain the reference solution. Reference substance: calibrated standard substance of the compound of formula I provided by Chengdu Shibeikang Biomedical Technology Co., Ltd.

Determination method: according to General Chapter 0512 High Performance Liquid Chromatography in *Chinese Pharmacopoeia* (2015 Edition) Volume IV, 10 μl of the test solution and 10 μl of the reference solution were accurately measured respectively, and injected into the liquid chromatograph to record chromatograms.

TABLE 1

Determination results of related substances in the crystalline forms in the examples

| No. | Content (%) | Maximum single impurity (%) | Diastereoisomer (%) | Number of impurities |
|---|---|---|---|---|
| Example 1 | 99.82 | <0.10 | <0.30 | 2 |
| Example 2 | 99.92 | <0.10 | <0.30 | 2 |
| Example 3 | 99.94 | <0.10 | <0.30 | 2 |
| Example 4 | 99.89 | <0.10 | <0.30 | 2 |
| Example 5 | 99.87 | <0.10 | <0.30 | 2 |
| Example 6 | 99.91 | <0.10 | <0.30 | 2 |
| Example 7 | 99.88 | <0.10 | <0.30 | 2 |
| Comparative preparation example 1 | 96.89 | >0.50 | >0.45 | 5 |
| Comparative preparation example 2 | 96.43 | >0.50 | >0.45 | 5 |
| Comparative preparation example 3 | 97.73 | >0.50 | >0.45 | 5 |

As can be seen from Table 1, the purities of the crystalline form B prepared by the method according to the present invention were all greater than 99%, and the maximum single impurity was less than 0.1%, which met ICH impurity requirements for active pharmaceutical ingredients (APIs), and the diastereomers were metabolites in vivo, and the criterion thereof could be relatively relaxed according to ICH impurity requirements. Compared with the crystalline forms prepared in comparative preparation examples, the crystalline form B prepared by the method according to the present invention had a higher content, a lower maximum single impurity content, and fewer impurities.

In accordance with ICH impurity requirements for APIs, the crystalline form of the compound prepared in each comparative preparation example did not meet the pharmaceutical requirements.

Test 2 Stability Investigation of the Crystalline Forms in the Examples

Samples of the crystalline form B from each Example and the crystalline form from each comparative preparation example were placed in an open and flat way to investigate 5-day stability and 10-day stability of the samples under the conditions of light (4500 Lux), heating at 40° C. and 60° C. and high humidity of 75% and 90%, respectively. The detection was carried out according to the determination method in Test 1, and HPLC purity detection results were shown in the table below.

TABLE 2

Determination results of the examples under the light (4500 Lux) condition

| No. | Day 0 (%) | Day 5 (%) | Day 10 (%) |
|---|---|---|---|
| Example 1 | 99.82 | 99.82 | 99.82 |
| Example 2 | 99.92 | 99.92 | 99.92 |
| Example 3 | 99.94 | 99.94 | 99.94 |
| Example 4 | 99.89 | 99.89 | 99.89 |
| Example 5 | 99.87 | 99.87 | 99.86 |
| Example 6 | 99.91 | 99.91 | 99.90 |
| Example 7 | 99.88 | 99.88 | 99.87 |
| Comparative preparation example 1 | 96.89 | 96.80 | 96.75 |
| Comparative preparation example 2 | 96.43 | 96.35 | 96.27 |
| Comparative preparation example 3 | 97.73 | 97.70 | 97.65 |

As can be seen from Table 2, the crystalline form B prepared in each example of the present invention and the crystalline form of the compound prepared in each comparative preparation example were relatively stable under the light (4500 Lux) condition, and in comparison, the crystalline form B prepared in each example of the present invention had better stability.

TABLE 3

Stability results under the condition of heating at 40° C.

| No. | Day 0 (%) | Day 5 (%) | Day 10 (%) |
|---|---|---|---|
| Example 1 | 99.82 | 99.82 | 99.81 |
| Example 2 | 99.92 | 99.92 | 99.91 |
| Example 3 | 99.94 | 99.93 | 99.93 |
| Example 4 | 99.89 | 99.89 | 99.88 |
| Example 5 | 99.87 | 99.87 | 99.87 |
| Example 6 | 99.91 | 99.91 | 99.90 |
| Example 7 | 99.88 | 99.88 | 99.88 |
| Comparative preparation example 1 | 96.89 | 96.31 | 95.35 |
| Comparative preparation example 2 | 96.43 | 96.01 | 94.78 |
| Comparative preparation example 3 | 97.73 | 97.22 | 96.13 |

As can be seen from Table 3, the crystalline form of the compound prepared in comparative preparation examples was more sensitive to temperature, and the crystalline form B prepared in each example of the present invention had significantly better stability than the crystalline form of the compound prepared in comparative preparation examples.

TABLE 4

Stability results under the condition of heating at 60° C.

| No. | Day 0 (%) | Day 5 (%) | Day 10 (%) |
|---|---|---|---|
| Example 1 | 99.82 | 99.79 | 99.77 |
| Example 2 | 99.92 | 99.87 | 99.84 |
| Example 3 | 99.94 | 99.90 | 99.88 |
| Example 4 | 99.89 | 99.87 | 99.86 |
| Example 5 | 99.87 | 99.85 | 99.85 |
| Example 6 | 99.91 | 99.89 | 99.88 |
| Example 7 | 99.88 | 99.85 | 99.84 |
| Comparative preparation example 1 | 96.89 | 95.45 | 94.37 |
| Comparative preparation example 2 | 96.43 | 95.23 | 93.89 |
| Comparative preparation example 3 | 97.73 | 96.60 | 95.23 |

As can be seen from Table 4, the crystalline form of the compound prepared in comparative preparation examples was more sensitive to high temperature, and the crystalline form B prepared in each example of the present invention had significantly better stability than the crystalline form of the compound prepared in comparative preparation examples.

TABLE 5

Stability results at high humidity of 90%

| No. | Day 0 (%) | Day 5 (%) | Day 10 (%) |
|---|---|---|---|
| Example 1 | 99.82 | 99.82 | 99.81 |
| Example 2 | 99.92 | 99.92 | 99.91 |
| Example 3 | 99.94 | 99.94 | 99.94 |
| Example 4 | 99.89 | 99.89 | 99.89 |
| Example 5 | 99.87 | 99.87 | 99.86 |
| Example 6 | 99.91 | 99.91 | 99.90 |
| Example 7 | 99.88 | 99.88 | 99.87 |
| Comparative preparation example 1 | 96.89 | 96.75 | 96.69 |
| Comparative preparation example 2 | 96.43 | 96.33 | 96.23 |
| Comparative preparation example 3 | 97.73 | 97.66 | 97.58 |

As can be seen from Table 5, the crystalline form of the compound prepared in comparative preparation examples was more sensitive to high humidity, and the crystalline form B prepared in each example of the present invention had significantly better stability than the crystalline form of the compound prepared in comparative preparation examples.

Test 3 Determination of melting point data

The crystalline form B of the compound of formula I prepared in example 1 was ground and heated to investigate the stability of the crystalline form, and melting point data were shown below:

TABLE 6

Melting point data of the examples

| Batch No. | Processing method | Melting range |
|---|---|---|
| Example 1 (crystalline form B) | Grinding for 10 minutes under nitrogen protection | 148.0-150.5° C. |
| | Heating at 80° C. for 12 hours under nitrogen protection | 148.2-150.3° C. |
| Comparative preparation example (crystalline form) | Grinding for 10 minutes under nitrogen protection | 135.0-138.0° C. |
| | Heating at 80° C. for 12 hours under nitrogen protection | 136.8-139.0° C. |

It is well known that the higher the stability of the crystalline form, the higher the melting point, and different melting points correspond to different crystalline forms. As can be seen from Table 6, the crystalline form B prepared in Example 1 of the present invention had a higher melting point than the crystalline form of the compound prepared in the comparative preparation examples, which further indicated that the crystalline form B had significantly better stability than the crystalline form of the compound prepared in the comparative preparation examples.

Test 4 Study on Tabletting Performance of the Examples

Test Method:

① After pulverization, raw materials were passed through a 80-mesh screen.

② The raw materials and excipients were weighed according to the above formula, and the raw materials were mixed with some lactose. A mixture of the raw materials and some lactose was mixed with remaining lactose, microcrystalline cellulose, corn starch and crospovidone homogeneously, and then mixed with magnesium stearate homogeneously.

③ Determination of material flowability

Determination method: An iron ring was fixed on an iron stand; a watch glass was placed directly below a funnel; the watch glass was adjusted so that an origin of the watch glass was perpendicular to the funnel; multiple batches of materials were slowly fed from the funnel until an edge of the watch glass could not hold the materials, i.e., forming a regular cone; feeding was stopped at that time; a height h of the materials was measured with a ruler; and then an outer diameter R of the watch glass was determined according to the equation tang$\theta$=2 h/R. The $\theta$ value was calculated to obtain an angle of repose.

TABLE 7

Formulation Composition

| Formulation Composition (g/1000 tablets) | Comparative preparation example 1 | Example 1 |
|---|---|---|
| Crystalline form of raw materials | Crystalline form of comparative preparation example | Crystalline form B |
| Compound of formula I (calculated on the basis of the pure compound of formula I, the same content) | 1 | 1 |
| Lactose | 90 | 90 |
| Microcrystalline cellulose | 20 | 20 |
| Corn starch | 10 | 10 |
| Crospovidone | 8 | 8 |
| Magnesium stearate | 1 | 1 |

TABLE 8

Determination results of the angle of repose of total mixed particles

| | Comparative preparation example 1 | Example 1 |
|---|---|---|
| Angle of repose | 38.3° ± 0.5 | 30.5° ± 0.7** |

Note:
Compared with the comparative preparation example, **P < 0.01.

Conclusion: The test results were shown in Table 8. The mixture prepared from the crystalline form in Example 1 had better flowability than the mixture prepared from the crystalline form in the comparative preparation examples, was more conducive to the control of tablet weight variation during tabletting, and was more conducive to the automatic and commercial production of tablets. The results indicated that the crystalline form B of Example 1 had a significant advantage in flowability (**P<0.01).

Test 5 Study on pharmacodynamics of the examples

Test method: Two tablets having the same content of the compound of formula I in different crystalline forms were prepared from the same type and weight of the excipients by the same powder tabletting process. One tablet was the tablet of the crystalline form B of Example 1, and the other tablet was the tablet of the crystalline form of the comparative preparation examples. The two tablets were compared in terms of anti-platelet aggregation effect.

Eight male beagles with a weight difference no more than 1 kg were randomly divided into two groups according to body weight, with four in each group, and administered in two cycles. In a first cycle, Example 1 group and the comparative preparation example group were both orally administered 30 mg (calculated as pure compound of formula I, the same content) tablets. Blood was taken from the beagles before and 6 hours after administration to collect platelet-rich plasma. Platelet aggregation was induced with 20 μM ADP, and the aggregation rate in the platelet-rich plasma was measured by a platelet aggregometer.

After 14 days of elution, the animals were crossed. Similarly, in a second cycle, Example 1 group and the comparative preparation example group were both orally administered 30 mg (calculated as pure compound of formula I, the same content) tablets. Blood was taken from the beagles before and 6 hours after administration to collect platelet-rich plasma. Platelet aggregation was induced with 20 μM ADP, and the aggregation rate in the platelet-rich plasma was measured by a platelet aggregometer.

The test results were shown in Table 9.

TABLE 9

Results of pharmacodynamic test of the examples (n = 8)

| Group | Administration Route | Dosage (single animal) | Platelet aggregation rate before administration (%) | Platelet aggregation rate after administration (%) |
|---|---|---|---|---|
| Tablet of Example 1 (crystalline form B) | Per os | 30 mg | 71.5 ± 13.7 | 4.50 ± 2.12* |
| Tablet of Comparative preparation example 1 (crystalline form) | Per os | 30 mg | 71.0 ± 12.9 | 8.31 ± 4.11 |

Note:
Compared with the comparative preparation example, **P < 0.05.

Conclusion: The test results were shown in Table 9. Compared with the comparative preparation example, there was no significant difference before administration, but 6 hours after administration, the crystalline form B of Example 1 had a more potent anti-ADP-induced platelet aggregation effect (*P<0.05), and had significant advantages. Therefore, the crystalline form B was a superior crystalline form with further development potential for medicinal use, and was worthy of further research.

The crystalline form B of methyl (S)-2-(2-chlorophenyl)-2-((S)-2-oxo-2,6,7,7a-tetrahydrothieno[3,2-c]pyridin-5(4H)-yl)acetate and the preparation method thereof as provided and disclosed in the present invention can be implemented by a person skilled in the art by appropriately changing the raw materials, process parameters and other aspects with reference to the contents herein. The methods and products of the present invention have been described by way of preferred embodiments thereof, and it will be apparent for a person skilled in the art to make modifications or appropriate changes and combinations to the methods and products described herein to implement the technology of the present invention without departing from the content, spirit and scope of the present invention. In particular, it should be noted that all similar substitutions and modifications will be obvious to a person skilled in the art, and they are all considered to be included within the spirit, scope and content of the present invention.

What is claimed is:

1. A crystalline form B of a tetrahydrothienopyridine compound of formula I, having characteristic peaks at 2θ angles of 11.21±0.2°, 12.61±0.2°, 14.69±0.2°, 16.14±0.2°, 17.81±0.2°, 20.22±0.2°, and 22.10±0.2° degrees in an X-ray powder diffraction pattern with Cu-Kα radiation,

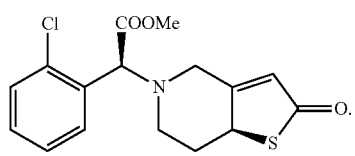

formula I

2. The crystalline form B of the tetrahydrothienopyridine compound according to claim 1, having characteristic peaks at 2θ angles of 11.21±0.2°, 12.61±0.2°, 14.69±0.2°, 16.14±0.2°, 17.81±0.2°, 20.22±0.2°, 22.10±0.2°, 23.24±0.2°, 27.68±0.2°, and 28.57±0.2° degrees in the X-ray powder diffraction pattern with Cu-Kα radiation.

3. The crystalline form B of the tetrahydrothienopyridine compound according to claim 2, having characteristic peaks at 2θ angles of 11.21±0.2°, 12.61±0.2°, 14.69±0.2°, 16.14±0.2°, 17.81±0.2°, 19.42±0.2°, 20.22±0.2°, 20.76±0.2°, 22.10±0.2°, 23.24±0.2°, 24.31±0.2°, 27.01±0.2°, 27.68±0.2°, 28.57±0.2°, and 31.09±0.2° degrees in the X-ray powder diffraction pattern with Cu-Kα radiation.

4. The crystalline form B of the tetrahydrothienopyridine compound according to claim 1, wherein the crystalline form has the X-ray powder diffraction pattern as shown in FIG. 1.

5. The crystalline form B of the tetrahydrothienopyridine compound according to claim 4, wherein the crystalline form has a differential scanning calorimetry spectrogram having an endothermic peak at 151.71±5° C.

Figure 2:
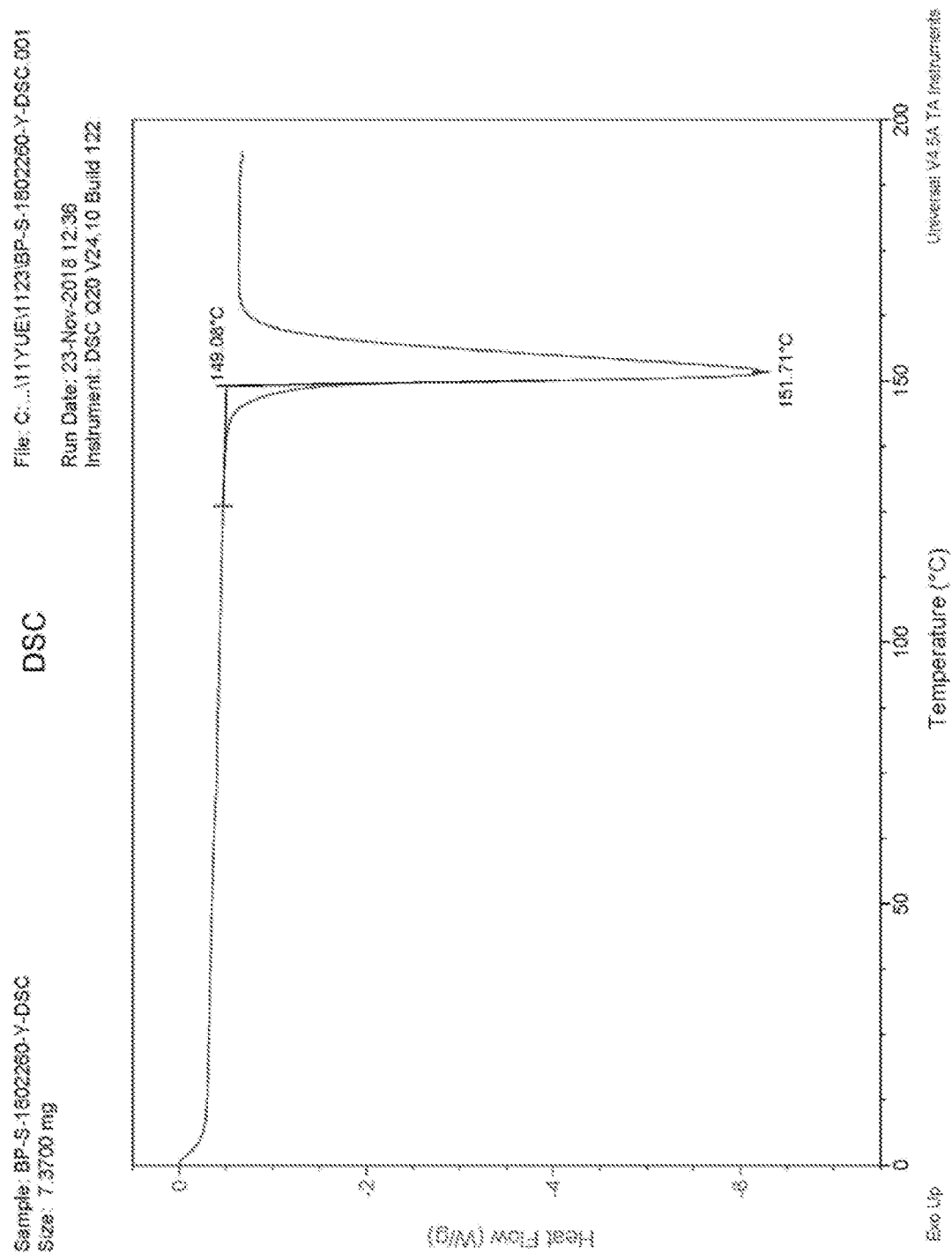
FIG. 2 shows a DSC spectrogram of the crystalline form B of the compound of formula I.

6. The crystalline form B of the tetrahydrothienopyridine compound according to claim 5, wherein the crystalline form has the differential scanning calorimetry spectrogram as shown in FIG. 2.

Figure 3:
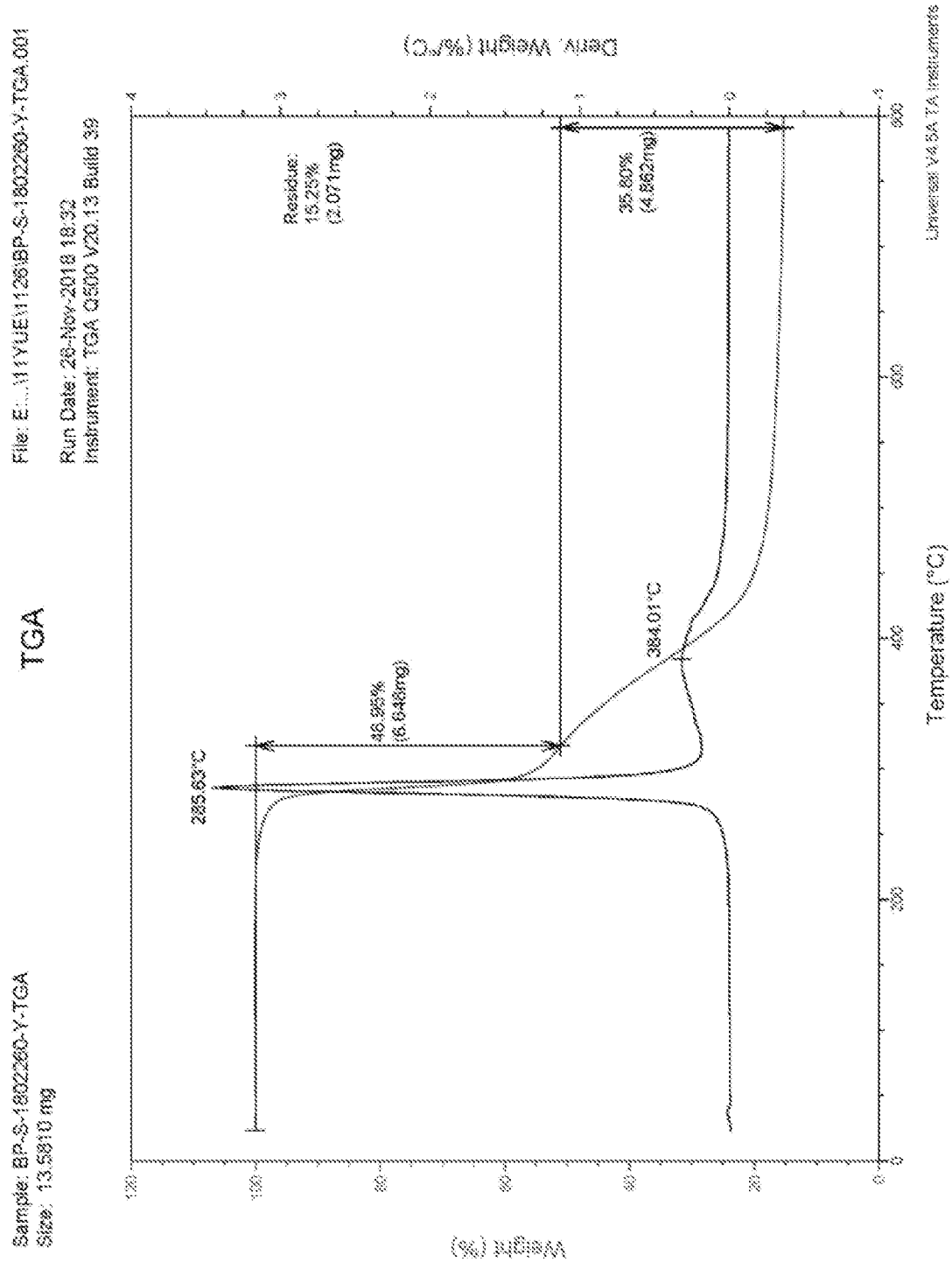
FIG. 3 shows a TGA spectrogram of the crystalline form B of the compound of formula I.

7. The crystalline form B of the tetrahydrothienopyridine compound according to claim 6, wherein the crystalline form has a thermogravimetric analysis spectrogram as shown in FIG. 3.

8. A method for preparing the crystalline form B of the tetrahydrothienopyridine compound according to claim 1, comprising dissolving a crude product of the compound of formula I in any crystalline form or amorphous form in a solvent in any manner, then cooling or concentrating to crystallize, filtering, washing and drying the resulting crystal to obtain the crystalline form.

9. A pharmaceutical composition, comprising a crystalline form B of a tetrahydrothienopyridine compound of formula I and one or more pharmaceutically acceptable carriers, wherein the crystalline form B has characteristic peaks at 2θ angles of 11.21±0.2°, 12.61±0.2°, 14.69±0.2°, 16.14±0.2°, 17.81±0.2°, 20.22±0.2°, and 22.10±0.2° degrees in an X-ray powder diffraction pattern with Cu-Kα radiation,

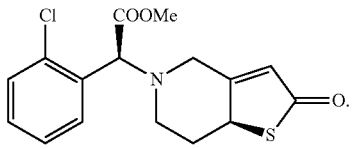

formula I

10. A method for treating cardiac, cerebral and other arterial circulation disorders due to platelet hyperaggregation in a subject, comprising administering to the subject in need thereof a crystalline form B of a tetrahydrothienopyridine compound of formula I, or a pharmaceutical composition comprising a crystalline form B of a tetrahydrothienopyridine compound of formula I and one or more pharmaceutically acceptable carriers, wherein the crystalline form B has characteristic peaks at 2θ angles of 11.21±0.2°, 12.61±0.2°, 14.69±0.2°, 16.14±0.2°, 17.81±0.2°, 20.22±0.2°, and 22.10±0.2° degrees in an X-ray powder diffraction pattern with Cu-Kα radiation,

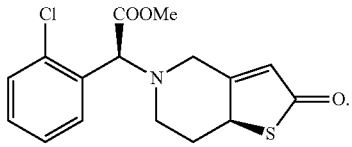

formula I

11. The crystalline form B of the tetrahydrothienopyridine compound according to claim 1, wherein a single crystal of the crystalline form B has a monoclinic crystal system having a space group P2₁, and has lattice constants a=6.7206(5)Å, b=15.2446(9)Å, c=8.0941(5)Å, α=90°, β=102.618(6)°, and γ=90°.

12. The crystalline form B of the tetrahydrothienopyridine compound according to claim 11, wherein the single crystal of the crystalline form B has an X-ray single crystal diffraction pattern as shown in FIG. 4.

13. The method according to claim 8, wherein a crude product of the compound of formula I is the crude product of the compound of formula I in a single isomer form.

14. The method according to claim 8, wherein the solvent is selected from any one or more of alcohols, ketones, nitriles, ethers, esters and sulfones with the number of carbon atoms less than 7 or equal to 7, or a mixed solvent of any one or more thereof and water.

15. The method according to claim 14, wherein the alcohols are selected from methanol, ethanol, isopropanol, 1-propanol, 2-propanol, 1-butanol, 2-butanol or pentanol; the ketones are selected from acetone, methyl ethyl ketone or methyl isopropyl ketone; the nitrile is acetonitrile; the ethers are selected from diethyl ether, isopropyl ether, methyl tert-butyl ether or anisole; the esters are selected from methyltetrahydrofuran, ethyl formate, ethyl acetate, propyl acetate, butyl acetate, isopropyl acetate or isobutyl acetate; and the sulfone is dimethyl sulfoxide.

16. The method according to claim 8, wherein the cooling crystallization is standing crystallization at −20° C. to room temperature.

17. The method according to claim 8, wherein the concentration crystallization is carried out at a temperature of 35° C.

18. The method according to claim 10, wherein the other arterial circulation disorders include stroke, acute coronary syndrome, atherosclerosis, myocardial infarction or confirmed peripheral arterial diseases.

* * * * *